(12) United States Patent
Antel et al.

(10) Patent No.: US 7,074,822 B2
(45) Date of Patent: Jul. 11, 2006

(54) ALKYL CARBAMATE-SUBSTITUTED β-LACTONES, PROCESS FOR THEIR PREPARATION, AND PHARMACEUTICAL COMPOSITIONS CONTAINING THEM

(75) Inventors: Jochen Antel, Bad Muender (DE); Sabine Eyting, Muenster (DE); Peter Colin Gregory, Hannover (DE); Harald Waldeck, Isernhagen (DE); Michael Wurl, Garbsen (DE); Maike Wolff, Hannover (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 10 days.

(21) Appl. No.: 11/062,599

(22) Filed: Feb. 22, 2005

(65) Prior Publication Data
US 2005/0197386 A1 Sep. 8, 2005

Related U.S. Application Data

(60) Provisional application No. 60/546,196, filed on Feb. 23, 2004.

(30) Foreign Application Priority Data
Feb. 23, 2004 (DE) .................. 10 2004 009 076

(51) Int. Cl.
*A61K 31/337* (2006.01)
*C07D 305/12* (2006.01)
(52) U.S. Cl. ...................... 514/449; 549/328
(58) Field of Classification Search ............... 514/449; 549/328
See application file for complete search history.

(56) References Cited

U.S. PATENT DOCUMENTS

| | | | |
|---|---|---|---|
| 4,175,186 A | 11/1979 | Rasheed et al. |
| 4,189,438 A | 2/1980 | Umezawa et al. |
| 4,358,602 A | 11/1982 | Umezawa et al. |
| 4,598,089 A | 7/1986 | Hadvary et al. |
| 4,806,564 A | 2/1989 | Chabala et al. |
| 4,931,463 A | 6/1990 | Barbier et al. |
| 5,245,056 A | 9/1993 | Karpf et al. |
| 5,376,674 A | 12/1994 | Derungs et al. |
| 5,399,720 A | 3/1995 | Karpf et al. |
| 5,466,708 A | 11/1995 | Derungs et al. |
| 5,986,132 A | 11/1999 | Reeve et al. |
| 6,235,305 B1 | 5/2001 | Mullins |
| 6,342,519 B1 | 1/2002 | Mullins |
| 6,348,492 B1 | 2/2002 | Mullins |
| 2001/0012852 A1 | 8/2001 | Mullins |
| 2002/0016307 A1 | 2/2002 | Mullins |
| 2002/0045767 A1 | 4/2002 | Mullins |
| 2003/0162961 A1 | 8/2003 | Coates et al. |
| 2003/0181433 A1 | 9/2003 | Schoenafinger et al. |

FOREIGN PATENT DOCUMENTS

| | | |
|---|---|---|
| DE | 31 09 335 A1 | 3/1982 |
| EP | 0 129 748 A1 | 1/1985 |
| EP | 0 293 132 A1 | 11/1988 |
| EP | 0 443 449 A2 | 8/1991 |
| EP | 0 444 428 A2 | 9/1991 |
| EP | 0 444 482 B1 | 9/1991 |
| JP | 3-115274 | 5/1991 |
| WO | WO 97/19050 A1 | 5/1997 |
| WO | WO 01/32669 A1 | 5/2001 |
| WO | WO 01/32670 A1 | 5/2001 |
| WO | WO 03/050154 A2 | 6/2003 |
| WO | WO 03/072555 A1 | 9/2003 |
| WO | WO 2004/065346 A1 | 8/2004 |

OTHER PUBLICATIONS

Silvia Cardani, et al., "Titanium Tetrachloride-Mediated Enantioselective Synthesis of Trans β-Lactones", Tetrahedron, 1992, pp. 5557-5564, vol. 48, No. 27, Pergamon Press Ltd. Printed in Great Britain, XP-002330603.
Scott G. Nelson, et al., "Catalytic Asymmetric Acyl Halide-Aldehyde Cyclocondensation Reactions of Substituted Ketenes", J. AM. Chem. Soc., 2004, pp. 14-15, vol. 126, American Chemical Society, XP-00230604.
Keith T. Mead, et al., "A New Approach to the Preparation of 2-Substituted Tetrahydrofurans with Alpha-Syn Selectivity", Tetrahedron Letters, 1989, pp. 6829-6832, vol. 30, No. 49, Pergamon Press Plc, XP-002330605.
Cunxing Zhao, et al., "A β-Lactone-Based Route to Cyclopentanes via Intramolecular Allyisilane Additions. An Unexpected Friedel-Crafts Allkylation." Tetrahedron Letters, 1997, pp. 6537-6540, vol. 38, No. 37, Elsevier Science Ltd., PII: S0040-4039(97)01529-3.
Hong Woon Yang, et al., "Studies of the Tandem Mukalyama Aldol-Lactonization (TMAL) Reaction: A Concise and Highly Diastereoselective Route to β-Lactones Applied to the Total Synthesis of the Potent Pancreatic Lipase Inhibitor, (-) Panclicin D", Tetrahedron, 1997, pp. 16471-16488, vol. 53, No. 48, Elsevier Science Ltd., PII: S0040-4020(97)01029-6.*

(Continued)

Primary Examiner—Bernard Dentz
(74) Attorney, Agent, or Firm—Crowell & Moring LLP

(57) ABSTRACT

Substituted β-lactones (oxetanones) corresponding to the formula I,

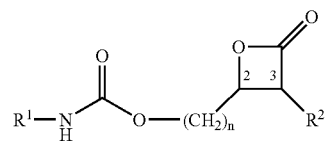

wherein $R^1$, $R^2$ and n have the meanings given in the specification, and pharmaceutical compositions which contain these compounds and have a pancreatic lipase-inhibiting action, as well as a process for the preparation of the compounds of Formula I and intermediate products of this process.

10 Claims, No Drawings

OTHER PUBLICATIONS

Makoto Oba, et al., "Radical-Based Deoxygenation of Aliphatic Alcohols via Thioxocarbamate Derivatives", Tetrahedron, 1994, pp. 10193-10200, vol. 50, No. 34, Elsevier Science Ltd., 0040-4020(94)00596-6.*

Eugen J. Verspohl, " Adipositas-Behandlung Beim Typ-2-Diabetiker".*

Masahiko Nishiyama, et al. "Addition Reaction and Deoxygenation of Alcohols Using Osothiocyanates and Triethyisilane-DTBP", Tetrahedron Letters, 1993, pp. 3745-3748, vol. 34, No. 23, Pergamon Press Ltd.*

Agnes Pommier, et al., "Recent Advances in β-Lactone Chemistry", Synthesis, 1993, pp. 441-459.*

Derek H. R. Barton, et al., "The Invention of Radical Reactions. 32. Radical Deoxygenations, Dehalogenations, and Deaminations with Dialkyl Phosphites and Hypophosphorous Acid as Hydrogen Sources", J. Org. Chem., 1993, pp. 6838-6842, vol. 58, American Chemical Society.*

* cited by examiner

ALKYL CARBAMATE-SUBSTITUTED β-LACTONES, PROCESS FOR THEIR PREPARATION, AND PHARMACEUTICAL COMPOSITIONS CONTAINING THEM

CROSS REFERENCE TO RELATED APPLICATIONS

This application claims priority from U.S. Provisional Patent Application No. 60/546,196, filed Feb. 23, 2004 and from Federal Republic of Germany Patent Application No. DE 10 2004 009 076.9, filed Feb. 23, 2004.

BACKGROUND OF THE INVENTION

The present invention relates to β-lactones (oxetanones) substituted by an unbranched alkyl carbamate side chain, which are suitable for the treatment and/or prophylaxis of obesity and also of associated accompanying and/or concomitant diseases in larger mammals and humans, in particular metabolic syndrome and cardiovascular diseases. Furthermore, the invention relates to pharmaceutical preparations containing these novel compounds and also to processes for the preparation of these compounds. The compounds according to the invention then act as inhibitors of lipase, in particular of pancreatic lipase.

Oxetanones substituted by a branched side chain and having an action inhibiting pancreatic lipase are already known from U.S. Pat. No. 5,260,310 (=EP 444,482).

Hexadecanoic acid and hexadecadienoic acid derivatives which inhibit pancreatic lipase and therefore can be used in combating or preventing obesity and hyperlipaemias are already known from U.S. Pat. No. 4,598,089 (=EP 129,748).

U.S. Pat. No.6,852,865 (=WO 03/050154) also describes, inter alia, oxetanones substituted by side chains as substrates for catalytic carbonylation.

SUMMARY OF THE INVENTION

It was an object of the present invention to provide new lipase-inhibitory compounds.

It was also an object of the invention to provide lipase-inhibitory substances suitable for the treatment and/or inhibition of obesity and accompanying and/or concomitant diseases.

Another object of the invention was to provide lipase inhibitory compounds which a highly effective mode of action.

A further object of the invention was to provide lipase-inhibitory compounds which can be obtained in simple manner.

These and other objects have been achieved in accordance with the present invention by providing a compound corresponding to formula I,

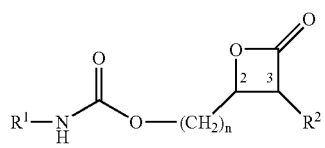

I wherein $R^1$ is $C_{1-18}$-alkyl, one or two alkyl-chain carbon atoms of which are optionally replaced by oxygen or sulfur; phenyl-$C_{0-18}$-alkyl, the phenyl group of which is optionally substituted one or two times by halogen, trifluoromethyl, nitro, $C_{1-8}$-alkyl, $C_{1-8}$-alkoxy, $C_{1-6}$-alkylcarbonyl, $C_{1-6}$alkoxycarbonyl, phenyl, benzyl or phenoxy, and one or two alkyl-chain carbon atoms of which are optionally replaced by oxygen or sulfur; $C_{3-7}$-cycloalkyl-$C_{0-18}$-alkyl, one or two alkyl-chain carbon atoms of which are optionally replaced by oxygen or sulfur, or benzoyl; $R^2$ is $C_{1-12}$-alkyl, one or two alkyl-chain carbon atoms of which are optionally replaced by oxygen or sulfur; phenyl-$C_{1-18}$-alkyl, the phenyl group of which is optionally substituted once or twice by halogen, $C_{1-4}$-alkyl, $C_{1-4}$-alkoxy, benzyl or phenoxy, and one or two alkyl-chain carbon atoms of which are optionally replaced by oxygen or sulfur; or $C_{3-7}$-cycloalkyl-$C_{0-18}$-alkyl, one or two alkyl-chain carbon atoms of which are optionally replaced by oxygen or sulfur, and n is a whole number from 2 to 8.

It has now been found that a group of alkyl carbamate-substituted β-lactones which are unbranched in the alkyl carbamate side chain can act as inhibitors of lipase, in particular of pancreatic lipase. The compounds according to the invention are thus capable of reducing the lipid digestion induced by pancreatic lipase in mammals, particularly humans, with the result that the body has overall fewer usable edible fats available. The compounds according to the invention therefore appear suitable for the treatment and/or prophylaxis of obesity and illnesses associated therewith.

The present invention relates to lipase-inhibitory alkyl carbamate-substituted β-lactones corresponding to formula I,

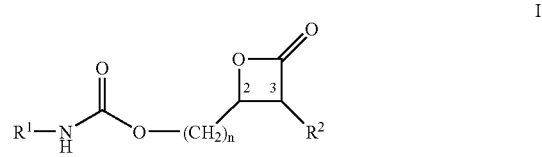

I wherein
$R^1$ is $C_{1-18}$-alkyl, the alkyl-chain carbon atoms of which are optionally replaced 1–2 times by oxygen and/or sulfur; phenyl-$C_{0-18}$-alkyl, the phenyl group of which is optionally substituted 1–2 times by halogen, trifluoromethyl, nitro, $C_{1-8}$-alkyl, $C_{1-8}$-alkoxy, $C_{1-6}$-alkylcarbonyl, $C_{1-6}$-alkoxycarbonyl, phenyl, benzyl and/or phenoxy and the alkyl-chain carbon atoms of which are optionally replaced 1–2 times by oxygen and/or sulfur; $C_{3-7}$-cycloalkyl-$C_{0-18}$-alkyl, the alkyl-chain carbon atoms of which are optionally replaced 1–2 times by oxygen and/or sulfur, or benzoyl;
$R^2$ is $C_{1-12}$-alkyl, the alkyl-chain carbon atoms of which are optionally replaced 1–2 times by oxygen and/or sulfur; phenyl-$C_{1-18}$-alkyl, the phenyl group of which is optionally substituted 1–2 times by halogen, $C_{1-4}$-alkyl, $C_{1-4}$-alkoxy, benzyl and/or phenoxy and the alkyl-chain carbon atoms of which are optionally replaced 1–2 times by oxygen and/or sulfur; or $C_{3-7}$-cycloalkyl-$C_{0-18}$-alkyl, the alkyl-chain carbon atoms of which are optionally replaced 1–2 times by oxygen and/or sulfur, and
n is a whole number from 2 to 8.

A further subject of the invention is medicaments containing the compounds of Formula I. Furthermore, a subject of the invention is a process for the preparation of the compounds of Formula I and intermediate products of this process.

Where in the compounds of Formula I or in other compounds described in the context of the present invention substituents are or contain alkyl, these may each be straight-chain or branched. Where substituents in compounds of Formula I stand for halogen, fluorine, chlorine or bromine are suitable. Chlorine is preferred.

$R^1$ is preferably phenyl-$C_{0-2}$-alkyl, the phenyl group of which is optionally substituted as stated above. Preferred substituents are $C_{1-4}$-alkyl, $C_{1-4}$-alkoxy and phenoxy. In particular, $R^1$ may stand for 4-phenoxyphenyl, benzyl, phenylethyl or 4-ethoxybenzyl. 4-phenoxyphenyl is particularly preferred.

$R^2$ is preferably $C_{2-6}$-alkyl, the alkyl-chain carbon atoms of which are optionally replaced 1–2 times by oxygen and/or sulfur, in particular hexyl. Where $R^2$ is phenyl-$C_{1-18}$-alkyl optionally substituted in the phenyl group, phenyl-$C_{2-4}$-alkyl is preferred.

n is preferably a whole number from 2 to 5.

Compounds of Formula I wherein the substituents of the carbon in the 2 position of the lactone ring and the substituents of the carbon in the 3 position of the lactone ring are in the trans position relative to each other are preferred.

Particularly preferred compounds of Formula I are selected from the group consisting of 5-(3-hexyl-4-oxo-oxetan-2-yl)-pentyl-(phenoxyphenyl)-carbamate and 4-(3-hexyl-4-oxo-oxetan-2-yl)-butyl-(phenoxyphenyl)-carbamate, each of which are particularly preferred in their 2S,3S-trans form.

Numerous processes for the preparation of β-lactones (oxetanes) are known (cf. e.g: A. Pommier, J.-M. Pons, Synthesis 5 (1993) 441–459). According to the invention, the novel compounds of Formula I are obtained by reacting a compound of the general formula II,

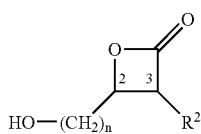

II wherein $R^2$ and n have the above meanings, with a compound of the general formula III,

R$^1$—N=C=O    III wherein $R^1$ has the above meaning.

The reaction of the alcohol derivative of Formula II with an isocyanate compound of Formula III can be carried out in known manner, for example in a solvent which is inert under the reaction conditions such as a dipolar-aprotic solvent, in particular a lower-alkyl halide, preferably dichloromethane. Usual reaction temperatures are between approximately −25° C. and approximately 50° C. Usually the reaction temperature during the addition of the reaction partners is kept between approximately −25° C. and 10° C., preferably 0° C., and once they have been completely added is increased to approximately 15° C. to 50° C., preferably room temperature (=RT). In some cases it is beneficial, after a certain reaction time, for example after 2 hours, to add to the reaction mixture a non-nucleophilic base, for example an organic nitrogen base such as in particular diisopropylethylamine (="Hünig's base"), and then to allow it to react further for a certain time, for example another 2 hours, to complete the reaction. Compounds of Formula I can then be isolated from the reaction mixture in known manner and if necessary purified.

Compounds of Formula II can be obtained by cleaving off the alcohol protective group from lactone compounds protected at the alcohol function of the general formula IVa,

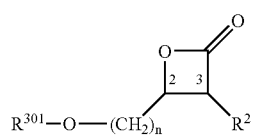

IVa wherein $R^2$ and n have the above meanings and $R^{301}$ stands for an alcohol protective group, in known manner. Suitable protective groups for alcohol functions and methods for the introduction and cleavage thereof are known for example from McOmie, "Protective Groups in Organic Chemistry", Plenum Press, and Greene, Wuts, "Protective Groups in Organic Synthesis", Wiley Interscience Publication, the newest edition of each. Particularly suitable alcohol protective groups $R^{301}$ are selected from the group consisting of benzyl, tetrahydropyranyl, methoxymethyl (=MOM), methoxyethoxymethyl (=MEM) and the silyl alcohol protective groups, in particular tert.butyidimethylsilyl and triethylsilyl.

Compounds of Formula II are novel compounds which are advantageously suitable as intermediate products for the preparation of novel pharmacologically active active substances, for example for the preparation of the compounds of Formula I.

Compounds of Formula III are known per se or can be prepared in known manner from known compounds.

Compounds of Formula IVa are novel compounds which are advantageously suitable as intermediate products for the preparation of novel pharmacologically active active substances, for example for the preparation of the compounds of Formula I. Compounds of Formula IVa, in particular the compounds 3-hexyl-4-{5[(tetrahydro-2H-pyran-2-yl)oxy]pentyl}oxetan-2-one and 3-hexyl-4-[5(benzyloxy)pentyl}]oxetan-2-one, likewise already exhibit an action inhibiting pancreatic lipase and therefore likewise appear advisable for the treatment and/or prophylaxis of obesity and its accompanying and/or concomitant diseases. The alcohol protective groups $R^{301}$ can be cleaved off again from compounds of Formula IV in known manner in order to obtain the free alcohol functions. In this manner, compounds of the general formula IV are accessible,

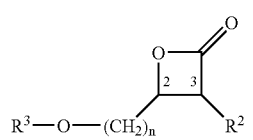

IV wherein $R^2$ and n have the above meanings and $R^3$ is hydrogen or an alcohol protective group.

Compounds of Formula IVa can be obtained, in a first variant, by cyclising a β-hydroxycarboxylic acid of the general formula V,

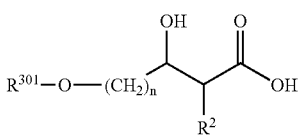

wherein $R^2$, $R^{301}$ and n have the above meanings, in known manner to form a β-lactone. The cyclisation can for example be performed by reacting the compound of Formula IVa with a reagent which together with a carboxylic acid function produces a readily cleavable leaving group, such as with a sulfonic acid derivative, for example with toluene sulfonic acid chloride. Likewise it is also possible, in a compound of Formula IVa in known manner to activate the free alcohol function accordingly, in order to make it accessible to the nucleophilic attack of the optionally activated carboxylic acid function, for example the carboxylate.

Compounds of Formula V can be prepared in a first variant by reacting an aldehyde of the general formula VI,

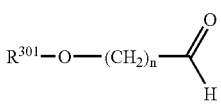

wherein $R^{301}$ and n have the above meanings, in known manner with a carboxylic acid derivative of the general formula VII,

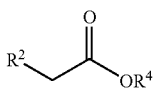

wherein $R^2$ has the above meaning and $R^4$ is hydrogen or $C_{1-4}$-alkyl. To perform the reaction, a compound of Formula VII may first be—optionally doubly—deprotonated in known manner with a strong non-nucleophilic base such as lithium diisopropylamide (=LDA), and the resulting carbanion can then be reacted with the compound of Formula VI. The compounds of Formula V prepared according to this aforementioned variant as a rule do not have a defined stereochemistry at the carbon atoms bearing the substituents "$R^2$" and "β-hydroxy", and are therefore present as "syn/anti-mixtures".

Aldehydes of Formula VI can be prepared by known selective oxidation of primary alcohols of the general formula VIII,

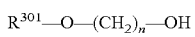

wherein $R^{301}$ and n have the above meanings. The selective oxidation may for example be performed as what is called a "Swern oxidation", with dimethyl sulfoxide (=DMSO) being used as oxidising agent in the presence of an electrophile, for example oxalyl chloride. Furthermore, selective oxidation can also be performed with pyridinium chlorochromate (=PCC) as oxidising agent. Compounds of Formula VIII are known per se or can be prepared in known manner, in particular by known introduction of suitable alcohol protective groups into the corresponding basic terminal diols.

Compounds of Formula VII are known per se, or can be prepared in known manner from known compounds.

Compounds of Formula V can also be prepared in a second variant by first doubly deprotonating a compound of the general formula IX,

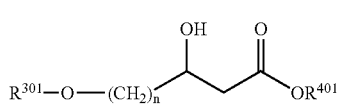

wherein $R^{301}$ and n have the above meanings and $R^{401}$ is $C_{1-4}$-alkyl, in particular methyl, in known manner with a strong non-nucleophilic base such as a lithium-lower-alkyl compound, preferably LDA, and then reacting the deprotonated intermediate product with a compound of the general formula X, $$R^2—X \qquad \qquad X$$

wherein $R^2$ has the above meaning and X stands for a cleavable leaving group, for example halogen, in particular iodine, bromine or chlorine, preferably iodine, and subsequently cleaving off the ester group $R^{401}$ in known manner. The deprotonation and the subsequent reaction with a compound of Formula X can be carried out in an organic solvent which is inert under the reaction conditions, such as a di-lower alkyl ether, in particular tetrahydrofuran (=THF). In a preferred variant, compounds of Formula V can be obtained at least in diastereomer-enriched form, preferably diastereoselectively, if a suitable complexing agent is added to the reaction mixture before the compound of Formula X is added. Suitable complexing agents are for example tris-(dimethylamino)-phosphine (=HMPT), 1,3-dimethyl-3,4,5,6-tetrahydro-2(1H)-pyrimidinone (=DMPH) or 1,3-dimethyl-imidazolidin-2-one (=DMEU). DMPH is preferred. The compounds of Formula V under these conditions are preferentially formed in the "anti" configuration. The aforementioned cleavage of the ester group $R^{401}$ can for example be carried out by saponification with an alkali hydroxide such as lithium hydroxide and in a polar-protic solvent such as ethanol.

Compounds of Formula IX can be prepared in a first variant by first deprotonating in known manner a compound of the general formula XI,

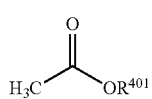

wherein $R^{401}$ has the above meaning, with a strong, non-nucleophilic base such as a lithium-lower-alkyl compound, preferably LDA, and then reacting the deprotonated intermediate product with a compound of Formula VI. The deprotonation and the subsequent reaction with a compound of Formula VI can be performed in an organic solvent which is inert under the reaction conditions, such as a di-lower alkyl ether, in particular THF. Operation is usually at low temperatures of between about −80° C. and −50° C.

Compounds of Formula XI are known or can be prepared in known manner from known compounds.

Compounds of Formula IX can be prepared in a second variant in at least enantiomer-enriched form, preferably enantiomerically pure form, by selectively oxidising a racemic starting compound of Formula IX in known manner to form a β-keto ester of the general Formula XII,

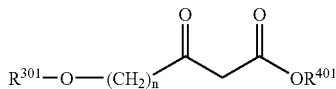

XII wherein $R^{301}$, $R^{401}$ and n have the above meanings, and then selectively reducing the resulting keto ester compound in the presence of a suitable chiral catalyst to form an at least enantiomer-enriched compound of Formula IX. The oxidation of a starting compound of Formula IX can be carried out in an organic solvent which is inert under the reaction conditions such as a lower-alkyl halide, in particular dichloromethane. PCC, for example, is suitable as selective oxidising agent. The enantioselective reduction of a β-keto ester of the general formula XII can be carried out with air excluded in a solvent which is inert under the reaction conditions, such as dimethyl formamide (=DMF) or methanol or in a mixture of the aforementioned solvents. The hydrogenation can be performed at a hydrogen pressure of approximately 2–6 bar, preferably approximately 4.0–4.5 bar. Suitable reaction temperatures are between approximately 50° C. and approximately 90° C., preferably between approximately 60° C. and 80° C. Suitable chiral hydrogenation catalysts are in particular known complexes of ruthenium-II with (S)-(-)-2,2'-bis-(diphenylphosphino)-1,1'-binaphthyl (=(S)-(-)-BINAP) or of ruthenium-II with (R)-(+)-2,2'-bis-(diphenylphosphino)-1,1'-binaphthyl (=(R)-(+)-BINAP). Depending on the stereochemistry in the chiral hydrogenation catalyst, a compound of Formula IX which is enriched in each case at least in (S)-isomer or in (R)-isomer can be obtained. Where (S)-(-)-BINAP is used as ligand of the chiral catalyst, as a rule compounds of Formula IX are obtained, wherein the carbon bearing the newly produced alcohol function is in the "S" configuration.

Compounds of Formula IVa can also be obtained, in a second variant, by reacting in known manner a silyl-ketene acetal compound of the general formula XIII,

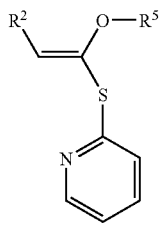

XIII wherein $R^2$ has the above meaning and $R^5$ is a silyl group, in particular triethylsilyl, in the manner of a Tandem-Mukaiyama-Aldol lactonisation (cf. e.g. H. W. Yang et al., Tetrahedron 53 No. 48 (1997) 16471–16488) with an aldehyde of Formula VI. The reaction can for example be carried out under a protective gas atmosphere in an organic solvent such as a lower-alkyl halide, in particular dichloromethane, and in the presence of a Lewis acid, in particular a Zn(II) salt such as Zn(II) chloride. In this reaction variant, as a rule mixtures of compounds of Formula IVa are obtained, the substituents "$R^2$" and "$R^{301}$—O—$(CH_2)_n$—" of which are predominantly in the "trans"-configuration relative to one another.

Compounds of Formula XIII can be prepared by deprotonating a compound of the general formula XIV,

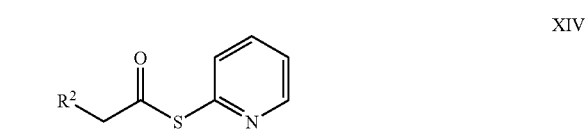

XIV wherein $R^2$ has the above meaning, in known manner first with a strong non-nucleophilic base, and then reacting the deprotonated intermediate product with a reagent suitable for introducing a silyl protective group. The reaction can be carried out in an organic solvent such as DMF or THF or in a mixture of these solvents. Lithium hexamethyl disilazide for example is suitable as strong non-nucleophilic base. Preferably the reaction is carried out at temperatures between approximately −90° C. and −60° C. For example triethylsilyl chloride can be used as reagent suitable for introducing a silyl protective group.

Compounds of Formula XIV can be obtained by reacting in known manner a compound of the general formula XV,

XV wherein $R^2$ and X have the above meanings, with 2-mercaptopyridine.

The compounds of Formula I contain two chiral carbon atoms, namely the carbon bearing the substituent "$R^1$—N—C(O)—$(CH_2)_n$—" in the 2 position of the lactone ring and the carbon bearing the substituent "—$R^2$" in the 3 position of the lactone ring. The compounds can thus be present in a total of four stereoisomeric forms. The present invention comprises both the mixtures of stereoisomers and enantiomers, and also the isomerically pure compounds of Formula I. Isomerically pure compounds of Formula I are preferred, in particular those in which the aforementioned substituents of the carbon atoms in the 2 position and in the 3 position of the lactone ring are in the "trans" configuration. Usually compounds of Formula I in which the carbon bearing the substituent "$R^1$—N—C(O)—$(CH_2)_n$—" in the 2 position of the lactone ring and the carbon bearing the substituent "—$R^2$" in the 3 position of the lactone ring are both in the "S" configuration are particularly preferred.

In the reactions described above, the optionally preformed chiral centres in the starting compounds of Formula V are no longer changed to compounds of Formula I in the subsequent reactions, so that depending on the type of starting compounds finally isomerically pure compounds of Formula I or isomer mixtures can be obtained. For the preparation of stereochemically uniform compounds of Formula I, expediently stereochemically uniform compounds of Formula V are used. If mixtures of isomers of Formula I are obtained, these may if desired be separated in known manner, for example by chromatography, in particular by HPLC separation on optionally chiral separating materials.

The compounds of Formula I according to the invention are suitable for the inhibition of lipase, in particular for the optionally selective inhibition of pancreatic lipase of larger mammals, particularly humans. Compounds with lipase-inhibiting properties are capable, if supplied to the digestive tract preferably together with fat-containing food, of reducing the proportion of edible fats actually digested by the body in the total edible fats ingested. In this manner, fat resorption in mammals, particularly humans, can be reduced. The group of compounds according to the invention thus appears suitable for the treatment and/or prophylaxis of obesity and of associated accompanying and/or concomitant diseases involved therewith. The accompanying diseases of obesity or the concomitant diseases thereof which can each be treated with the compounds according to the invention include in particular metabolic syndrome and cardiovascular diseases. The term "metabolic syndrome" usually covers a complex of clinical pictures which mainly comprise hypertension, in particular arterial hypertension, insulin resistance, in particular Type II diabetes mellitus, dyslipoproteinaemia, in particular as hypertriglyceridaemia, occurring as dyslipoproteinaemia accompanied by lowered HDL-cholesterol, and also hyperuricaemia, which can lead to gout. The term "cardiovascular diseases" in conjunction with obesity is usually understood to mean coronary heart disease, which can lead to heart failure, cerebrovascular diseases, which may for example be accompanied by an increased risk of strokes, and peripheral occlusive arterial disease. Further accompanying and/or concomitant diseases of obesity may be gall-bladder diseases such as formation of gallstones, sleep apnoea syndrome, orthopaedic complications such as osteoarthritis and psychosocial disorders.

Description of the Pharmacological Test Methods 1. p-nitrophenyl Palmitate Test

The lipase-inhibiting properties of the compounds of Formula I can be demonstrated e.g. by an in vitro activity test. In this test the inhibition of the lipolytic action of porcine pancreatic lipase with respect to the test substrate p-nitrophenyl palmitate(=pNpp) under the influence of the test substances of Formula I was determined. Therein, the change in the relative absorbance of the investigated solutions caused by the lipolytic release of p-nitrophenol from pNpp was measured.

The reagents given below were prepared:

A. Substrate Solution

To prepare a "solution A", 45 mg pNpp was dissolved in 15 ml isopropanol by sonication with ultrasound. To prepare a "solution B", 558 mg Na-deoxycholate dry substance and 67.5 mg gum arabic were dissolved in 135 ml 0.05 M sodium phosphate buffer (pH=8.0). 15 ml "solution A" was injected into 135 ml ice-cold "solution B" in 8 steps of 1.25 ml with an Eppendorf hand dispenser with stirring at 400 rpm at the highest possible rate. The initial absorbance E1 when determining the blank reading was less than 0.250 U each time.

B. Sodium Chloride Solution 1% (mN)

10 g sodium chloride (NaCl, p.a.) was dissolved in 1000 ml ultrapure water.

C. Lipase Standard Solution (50 FIP units/ml)

120.8 mg lipase standard LS7 in accordance with the rules of the "Fédération Internationale Pharmaceutique" (=FIP) (porcine pancreatic lipase, 36,700 FIP units/g) was dissolved in 50 ml ice-cold sodium chloride solution (B) and filtered through a 0.2 μm syringe filter. 20 ml of the filtrate was diluted with 8 ml sodium chloride solution (B) (corresponding to 50 FIP units/ml).

D. Lipase Calibration Solutions (10–20–30–40 FIP units/ml)

In each case 2–4–6–8 ml lipase standard solution (C) was made up to 10 ml with sodium chloride solution (B) and stored in an ice bath.

E. Lipase Stock Solution (40 FIP units/ml)

8 ml lipase standard solution was made up to 10 ml with sodium chloride solution (B) and stored in an ice bath.

F. Inhibitor Solutions

The lipase-inhibitory compounds of Formula I were dissolved in DMSO. A dilution series of 100–0.1 nmol/ml was produced from this stock solution. 100 μl of these dilutions were used in the test. The dilutions were adapted such that the maximum residual activity of the lipase was >90%.

G. Performance

Measurement was effected at 37° C., and the absorbances were measured at a wavelength of 405 nm. The photometric measuring station comprised a photometer and an agitator (from Eppendorf). The photometer was adjusted to 0 U with water. At the start and end of the investigation series, in each case eight blank readings and one lipase calibration series were measured. For the blank readings, in each case 1 ml substrate solution was mixed with 100 μl DMSO, the mixture was shaken for 5 seconds and kept at a controlled temperature for 5 minutes. Then 100 μl sodium chloride solution (B) were added thereto by pipette and the mixture was shaken for a further 5 seconds. After 2 minutes, the increase in absorbance was detected for 4 minutes. The absorbance starting value E1 when determining the blank readings was in each case less than 0.250 U.

For the calibration, 1 ml substrate solution was placed in each of eight cuvettes, mixed with 100 μl DMSO, shaken for 5 seconds and kept at a controlled temperature for 5 minutes. The reaction was started with 100 μl calibration solution. After 2 minutes, the kinetics were detected for 4 minutes. Each concentration was measured twice.

For measuring the inhibitor solutions, 1 ml substrate solution was placed in each of eight cuvettes, mixed with 100 μl inhibitor solution, shaken for 5 seconds and then kept at a controlled temperature for 5 minutes. The reaction was started with 100 μl lipase stock solution. After 2 minutes, the kinetics were detected for 4 minutes. The inhibitor solutions and the lipase standard solution were each prepared immediately before the start of the investigation series.

To calculate the results, the linear equation, the intercept and the coefficient of determination were determined from the calibration data and the blank reading by means of linear regression in accordance with the following equation:

$$y = mx + b$$

x=lipase units FIP units; y=absorbance in $\Delta$U/min; m=gradient in $(\Delta U/min)/U$; b=intercept The unknown activity x of a lipase inhibitor solution was calculated from these data in accordance with the following formula:

$$x = (y - b)/m$$

The following formula was used for the enzymatic residual activity [in %]:

$$\% = x * 100/4 \; FIP \; units$$

The measure of the inhibitory activity of the substances of Formula I which was determined was their $IC_{50}$ value. To this end, the inhibition values in percent measured for the individual compounds of Formula I were converted into concentrations and were converted into $IC_{50}$-values using the "PRISM-3" software in accordance with the following algorithm: non-linear curve fit, sigmoidal curve with variable gradient; 100% inhibition as maximum value, 0% inhibition as minimum value were added as constants. The $IC_{50}$ value of a test substance having enzyme-inhibitory activity is that concentration of the test substance at which the enzyme is still at 50% residual activity under otherwise identical test conditions. In the above pancreatic lipase activity test, the test substances of Formula I listed in Table 1 below exhibited the $IC_{50}$ values given below. The example numbers quoted relate to the preparation examples given below.

TABLE 1

Porcine pancreatic lipase-inhibiting action of the test substances in vitro with respect to pNpp

| Example No. | $IC_{50}$ [nM] |
|---|---|
| 1 | 106 |
| 2 | 47 |
| 3 | 88 |
| 6 | 113 |
| 7 | 107 |
| 8 | 187 |
| 9 | 67 |
| 10 | 177 |
| 11 | 28 |
| 13 | 319 |

2. Olive Oil Test

The lipase-inhibiting properties of the compounds of Formula I can also be demonstrated by a further in vitro activity test. In a heterogeneous reaction, the inhibition of the lipolytic action of porcine pancreatic lipase was determined under the influence of the test substances of Formula I with respect to the triglycerides contained in the test substrate olive oil. The fatty acids released by the lipase were titrated with sodium hydroxide solution to pH 9.0.

The reagents given below were prepared:

A. Gum Arabic Solution 10% (m/V)

200 g gum arabic (Acaciae gummi in accordance with the specifications of the German Pharmacopeia (=DAB)/European Pharmacopeia (=Ph.Eur.) was dissolved in 2000 ml ultrapure water with stirring and if necessary centrifugation. The solution was stored at −20° C. in plastic vessels of capacity of 250 ml. The amount required per day was thawed as required.

B. Sodium Taurocholate Solution 8% (m/V)

8 g sodium taurocholate (FIP) was dissolved in 100 ml ultrapure water.

C. Buffer Solution 60.6 mg Tris(hydroxymethyl)aminomethane p.a. (Merck, No. 8382) and 234 mg sodium chloride (p.a.) were dissolved in 100 ml ultrapure water.

D. 0.1 N Sodium Hydroxide Solution

E. Olive Oil Emulsion 40 ml olive oil (DAB, room temperature), 330 ml gum arabic solution (A.) and 30 g ice (made from ultrapure water) were emulsified in a suitable mixer for 15 minutes. The emulsion was freshly prepared for the respective day of use.

F. Reagent Mixture 100 ml sodium taurocholate solution (B.), 400 ml buffer solution (C.) and 450 ml ultrapure water were mixed with stirring. The mixture was prepared freshly each day. 19 ml was required for each measurement.

G. Lipase Solvent 10.0 g sodium chloride (p.a.), 6.06 g tris(hydroxymethyl)aminomethane (p.a. Merck, No. 8382) and 4.9 g maleic anhydride (p.a.) were dissolved in 900 ml ultrapure water. A pH value of 7.0 was set with 4 N sodium hydroxide solution (p.a.). The solution was made up to 1000.0 ml with ultrapure water. Storage at 5° C.+/−3° C. for up to 3 months.

H. Inhibitor Stock Solutions 5 ml of a 0.02 mM stock solution in DMSO was prepared from the inhibitor compounds of Formula I in each case. Then dilutions in a concentration range from 20,000–0.00002 nmol/test were produced from the stock solution. Aliquots of these solutions were used in the test. The dilutions and volumes in the test were adapted such that the maximum residual activity of the lipase was >90%.

I. Reference Suspension (Lipase Reference Standard)

Approx. 2500 FIP/Ph.Eur. units lipase reference standard were weighed accurately into a beaker, formed into a paste with some marine sand and a few drops of ice-cold lipase solvent (G.) using a glass rod, and the paste was stirred with 200 ml ice-cold lipase solvent for 15–30 min. in an ice bath. 1 ml of this solution was used in the test.

J. Reaction Solution 10 ml olive oil emulsion (E.) and 19 ml reagent mixture (F.) were kept at a controlled temperature in a thermostatted reaction vessel at 37.0° C.+/−0.1° C. The pH value was pre-adjusted to pH 9.0 with 0.1 mol/l sodium hydroxide solution (D.).

K. Lipase Inhibitor Solution 1 ml lipase reference suspension was incubated with the respective amount of inhibitor solution for 10 minutes in an ice bath. After the incubation period, the lipase inhibitor solution was pipetted into the reaction solution. This started the reaction. The acid released was titrated at 37.0° C.+/− 0.5° C. under pH-stat conditions at pH 9.0 automatically with 0.1 mol/l sodium hydroxide solution (D.) for at least 5 minutes. The sodium hydroxide consumption between the 1st and the 5th minute was evaluated. The titration was performed twice per inhibitor concentration and the results of both determinations were averaged. Likewise, the titration was carried out without addition of inhibitor solution, in order to determine the activity of the reference suspension. In order to calculate the lipase residual activity in relation to the lipase reference standard in FIP/Ph.Eur units per gramme when using inhibitors, the following equation was used:

$$[(n_u \times m_r)/(n_r \times m_u)] \times A = \text{lipase units/g}$$

$n_u$=ml consumption of 0.1 mol/l sodium hydroxide solution/min. upon titration of the lipase inhibitor test suspension $n_r$=ml consumption of 0.1 mol/l sodium hydroxide solution/min. upon titration of the reference suspension $m_u$=weight of the lipase reference standard in the test suspension with inhibitor in mg $m_r$=weight of the lipase reference standard in the reference suspension in mg A=declared activity of the reference standard in the reference suspension in FIP/Ph.Eur/g standard The result is given in "percent residual activity":

Residual activity [%]=lipase-*FIP/Ph.Eur* units/g×
100/desired activity of the reference standard The desired activity of the lipase reference standard according to FIP is 36,700 lipase-FIP/Ph.Eur units/g.

The measure of the inhibitory activity of the substances of Formula I which was determined corresponding to the manner given above for the pNpp test was their $IC_{50}$ value. In the above pancreatic lipase activity test, the test substances of Formula I listed in Table 2 below exhibited the $IC_{50}$ values given below. The example numbers quoted relate to the preparation examples given below.

TABLE 2

Porcine pancreatic lipase-inhibiting action of the test substances in vitro with respect to triglycerides in olive oil

| Example No. | $IC_{50}$ [nM] |
|---|---|
| 1 | 17 |
| 15 | 75 |

The lipase-inhibiting properties of the compounds of Formula I can also be demonstrated by feeding tests on rats.

The compounds of Formula I may be administered in conventional pharmaceutical preparations. The doses to be used may vary individually and will naturally vary according to the type of condition to be treated and the substance used. In general, however, medicinal forms with an active substance content of 10 to 500 mg, in particular 50 to 250 mg, active substance per individual dose are suitable for administration to humans and larger mammals.

The compounds may be contained according to the invention, together with conventional pharmaceutical auxiliaries and/or excipients, in solid or liquid pharmaceutical preparations. Examples of solid preparations are preparations which can be administered orally, such as tablets, coated tablets, capsules, powders or granules. These preparations may contain conventional inorganic and/or organic pharmaceutical excipients, such as talcum, lactose or starch, in addition to conventional pharmaceutical auxiliaries, for example lubricants or tablet disintegrating agents. Liquid preparations such as suspensions or emulsions of the active substances may contain the usual diluents such as water, oils and/or suspension agents such as polyethylene glycols and the like. Other auxiliaries may additionally be added, such as preservatives, taste correctives and the like.

The active substances may be mixed and formulated with the pharmaceutical auxiliaries and/or excipients in known manner. For the preparation of solid medicament forms, the active substances may for example be mixed with the auxiliaries and/or excipients in conventional manner and may be wet or dry granulated. The granules or powder may be poured directly into capsules or be pressed into tablet cores in conventional manner.

The preparation examples for the preparation of compounds of the general formula I given below are intended to explain the invention further, without limiting its scope.

EXAMPLE 1 trans-(3-hexyl-4-oxo-oxetan-2-yl)-pentyl-(phenoxyphenyl)-carbamate

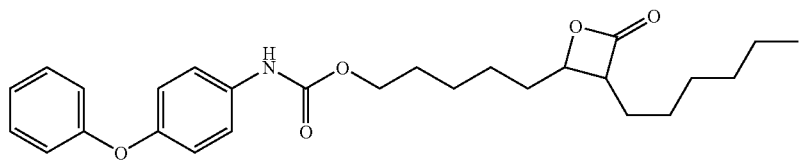

A) 18.9 g potassium tert.butylate was added in portions under a nitrogen atmosphere at 0° C. to a solution of 41.9 g 1,6-hexanediol in 400 ml dry DMF. After 15 minutes, a solution of 14 ml benzyl bromide in 120 ml dry DMF was added dropwise thereto at 0° C. The reaction mixture was stirred for 5 minutes at 0° C. and then for 2 hours at room temperature. The precipitate was filtered off and the filtrate was reduced in a vacuum. The residue was taken up in dichloromethane and washed in succession with water and saturated aqueous common salt solution. The organic phase was separated, dried over sodium sulfate and evaporated in a vacuum. The crude product was flash-chromatographed on silica gel with a solvent system consisting of n-hexane/ethyl acetate (4:1 v/v), with 19 g oily 6-(benzyloxy)hexan-1-ol being obtained, $^1$H-NMR (400 MHz, CDCl$_3$): δ=1.33–1.46 (m, 4H), 1.54–1.68 (m, 4H), 3.47 (t, 2H), 3.63 (t, 2H), 4.50 (s, 2H), 7.24–7.37 (m, 5H).

B) A solution of 25.1 ml DMSO in 50 ml dry dichloromethane was added dropwise under a nitrogen atmosphere to a solution of 14.8 ml oxalyl chloride in 250 ml dry dichloromethane at −55° C. After three minutes' stirring a solution of 24 g 6-(benzyloxy)hexan-1-ol in 100 ml dry dichloromethane was slowly added dropwise thereto at this temperature. After 15 minutes, 103 ml triethylamine was added dropwise thereto. Then the reaction mixture was stirred for 10 minutes at −55° C. and then warmed to room temperature (=RT). It was washed first with water and then with saturated aqueous common salt solution. The organic phase was separated, dried over sodium sulfate and evaporated in a vacuum. For purification, the crude product was flash chromatographed on silica gel with a solvent system of n-hexane/ethyl acetate (8:1 v/v), with 15.7 g 6-(benzyloxy)hexanal being obtained, $^1$H-NMR (400 MHz, CDCl$_3$): δ=1.38–1.46 (m, 2H), 1.59–1.70 (m, 4H), 2.43 (dt, 1H), 3.47 (t, 2H), 4.49 (s, 2H), 7.24–7.36 (m, 5H), 9.76 (t, 1H).

C) 104.2 ml of a 1.6-molar solution of butyllithium in n-hexane was added dropwise to a solution of 23.3 ml diisopropylamine in 200 ml THF under a nitrogen atmosphere at −70° C. Once this solution had been warmed to −20° C. and had been left for 10 minutes at this temperature, it was again cooled to −70° C. and 17.5 ml methyl acetate was slowly added dropwise thereto. After 15 minutes' stirring, a solution of 30.16 g 6-(benzyloxy) hexanal in 250 ml THF was added dropwise thereto at this temperature and the mixture was left for 10 minutes at −70° C. After slowly warming to −20° C., 150 ml of a saturated ammonium chloride solution was added and the mixture was diluted with ethyl acetate. After separating off the organic phase, the aqueous phase was extracted twice with ethyl acetate, and the combined organic extracts were washed with water and common salt solution. After drying over sodium sulfate, it was reduced in a vacuum and the crude product was flash-chromatographed with a solvent system of n-hexane/ethyl acetate (9:1 v/v) on silica gel, with 25.6 g 8-benzyloxy-3-hydroxy-octanoic acid-methyl ester being obtained after evaporation in a vacuum, $^1$H-NMR (400 MHz, DMSO-d6): δ=1.24–1.40 (m, 6H), 1.53 (m, 2H), 2.29 (dd, J=8.2; 14.7 Hz, 1H), 2.39 (dd, J=4.8; 14.7 Hz, 1H), 3.41 (t, 2H), 3.57 (s, 3H), 3.80 (m, 1H), 4.44 (s, 2H), 4.63 (d, J=5.7 Hz,1H), 7.24–7.37 (m, 5H).

D) 89.4 ml of a 1.6-molar solution of butyllithium in n-hexane was added dropwise to a solution of 14.3 ml diisopropylamine in 100 ml THF under a nitrogen atmosphere at −70° C. Once this solution had been warmed to −20° and had been left for 10 minutes at this temperature, it was cooled to −75° C. Then a solution of 18.0 g 8-benzyloxy-3-hydroxy-octanoic acid-methyl ester in 15 ml THF was added slowly thereto and the mixture was warmed to −45° C. over 2.5 hours. After cooling again to −70° C., 13.0 ml HMPT in 10 ml THF was added dropwise thereto and the mixture was stirred for 30 minutes. Then 30.4 g n-hexyl iodide was added thereto at −70° C. over a period of 30 minutes. This reaction mixture was warmed overnight to 10° C. For working-up, it was washed in succession with dilute aqueous potassium hydrogen sulfate solution and three times with water. Then the organic phase was dried over sodium sulfate and evaporated at reduced pressure. This test was repeated with 18.0 g 8-benzyloxy-3-hydroxy-octanoic acid-methyl ester. A total of 75 g crude product was obtained, which was flash-chromatographed with a solvent system of n-hexane/ethyl acetate (9:1 v/v), the composition of which was continuously changed to 3:1, on silica gel. 23.7 g diastereomerically pure 8-benzyloxy-3-hydroxy-octanoic acid methyl ester was obtained.

E) 25.33 g 8-benzyloxy-2-hexyl-3-hydroxy-octanoic acid methyl ester was dissolved in 180 ml ethanol and a solution of 5.2 g lithium hydroxide hydrate in 60 ml water was added thereto. This reaction mixture was stirred for 48 hours at RT. Then it was set to pH 6 with aqueous potassium hydrogen sulfate solution and evaporated at reduced pressure. The residue was taken up with EA, and washed in succession with aqueous potassium hydrogen sulfate solution, water and saturated aqueous common salt solution. The organic phase was separated, dried over sodium sulfate, evaporated in a vacuum and finally dried for 4 hours in an oil pump vacuum. 23.9 g 8-benzyloxy-2-hexyl-3-hydroxy-octanoic acid was obtained, IR: 2928, 2856, 1706, 1454, 1100 cm$^{-1}$.

F) 23.9 g 8-benzyloxy-2-hexyl-3-hydroxy-octanoic acid was dissolved in 100 ml pyridine under a nitrogen atmosphere and 13.3 g benzenesulfonic acid chloride was added thereto at −20° C. This reaction mixture was left to stand for 18 hours at 4° C. Then it was taken up with EA, the organic phase was washed in succession three times with water, dilute aqueous citric acid solution and saturated common salt solution, dried over sodium sulfate and evaporated at reduced pressure. This test was repeated with 5.76 g 8-benzyloxy-2-hexyl-3-hydroxy-octanoic acid. A total of 30 g crude product was obtained which was flash-chromatographed with a solvent system consisting of n-hexane/ethyl acetate (3:1 v/v) on silica gel, with a total of 21.4 g 4-[5-(benzyloxy)pentyl]-3-hexyl-oxetan-2-one being obtained as pure trans product, IR: 2929, 2857, 1818, 1455,1117 cm$^{-1}$.

G) 10.0 g of the product obtained above was dissolved in 200 ml ethyl acetate, and 1.0 g of a 10%-strength Pd/C catalyst was added thereto. Then it was hydrogenated for 4 hours at 2.5 bar hydrogen pressure. Once the catalyst had been filtered off, the organic phase was evaporated in a vacuum and 7.1 g 3-hexyl-4-(5-hydroxypentyl)-oxetan-2-one was obtained as pure trans product, $^1$H-NMR (400 MHz, CDCl$_3$): δ=0.89 (t, 3H), 1.2–1.9 (m, 18H), 3.17 (m, 1H), 3.66 (t, 2H), 4.22 (m, 1H).

H) A solution of 5.5 g 3-hexyl-4-(5-hydroxypentyl)-oxetan-2-one in 25 ml dichloromethane was added dropwise under a nitrogen atmosphere to a solution of 5.8 g 4-phenoxyphenyl isocyanate in 50 ml dichloromethane at 0° C. and was left for 5 minutes at 0° C. Then it was stirred for 2 hours at RT and 0.4 ml diisopropylethylamine (="Hünig's base") was additionally added to complete the reaction. After stirring overnight, the reaction mixture was washed first with water, then with saturated aqueous common salt solution. Then the organic phase was dried over sodium sulfate and evaporated in a vacuum. The remaining residue was flash-chromatographed on silica gel, with initially pure n-hexane, to which a continuously increasing proportion of ethyl acetate was added, being used as mobile solvent. After evaporating the product fractions in a vacuum, a solid residue was obtained which was recrystallised from n-hexane/EA. 7.1 g of the title compound was obtained as pure trans product, mp. 63.1–66.3° C.; $^1$H-NMR (400 MHz, CDCl$_3$): δ=0.89 (t, 3H), 1.2–1.9 (m, 18H), 3.17 (m, 1H), 4.17 (t, 2H), 4.22 (m, 1H), 6.55 (s, br, 1H), 6.96–7.00 (m, 4H), 7.07 (dt, 1H), 7.28–7.37 (m, 4H).

EXAMPLE 2 cis/trans-5-(3-hexyl-4-oxo-oxetan-2-yl)pentyl-phenyl carbamate

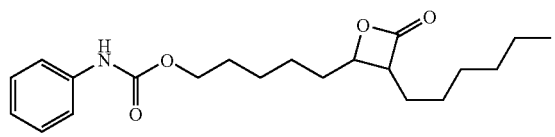

A) 16.3 g imidazole was added to a solution of 20.9 g 1,6-hexanediol in 300 ml DMF. A solution of 17.8 g tert.butyldimethylsilyl chloride in 120 ml DMF was added dropwise thereto at RT. Then it was stirred for 20 hours. Water was added thereto and the aqueous phase was extracted several times with EA. The combined organic phases were washed in succession with water and with saturated aqueous common salt solution, dried over sodium sulfate and evaporated in a vacuum. The remaining residue was flash-chromatographed with a solvent system consisting of n-hexane/ethyl acetate (9:1 v/v) on silica gel. 17.4 g 6-{[tert.butyl(dimethyl)silyl]oxy}hexan-1-ol was obtained, $^1$H-NMR (400 MHz, CDCl$_3$): δ=0.05 (s, 6H), 0.89 (s, 9H), 1.37 (m, 4H), 1.55 (m, 4H), 3.61 (t, 2H), 3.64 (t, 2H).

B) A solution of 15.9 ml DMSO in 75 ml dry dichloromethane was added dropwise under a nitrogen atmosphere to a solution of 9.4 ml oxalyl chloride in 250 ml dry dichloromethane at −55° C. After three minutes' stirring, a solution of 17 g 6-{[tert.butyl(dimethyl)silyl]oxy}hexan-1-ol in 150 ml dry dichloromethane was slowly added dropwise thereto at this temperature. After 15 minutes, 65.9 ml triethylamine was added dropwise. The reaction mixture was then stirred for 15 minutes at −55° C. and then warmed to RT. The organic phase was washed in succession with water and with saturated aqueous common salt solution. The organic phase was separated, dried over sodium sulfate, filtered off and evaporated in a vacuum. The remaining residue was flash-chromatographed with a solvent system of n-hexane/ethyl acetate (9:1 v/v) on silica gel, with 14.9 g 6-{[tert.butyl(dimethyl)silyl]oxy}hexanal being obtained, $^1$H-NMR (400 MHz, CDCl$_3$): δ=0.04 (s, 6H), 0.89 (s, 9H), 1.38 (m, 2H), 1.54 (m, 2H), 1.65 (m, 2H), 2.43 (dd, J=1.8; 7.3 Hz, 1H), 3.61 (t, 2H), 9.77 (t, J=1.8 Hz, 1H).

C) 113.4 ml of a 1.6 molar solution of n-butyllithium in n-hexane was added dropwise to a solution of 25.5 ml diisopropylamine in 300 ml THF at −70° C. Once this solution had been warmed to 0° C. and had been left for 10 minutes at this temperature, it was cooled to −50° C. and a solution of 14.2 ml octanoic acid in 150 ml THF was slowly added dropwise thereto at this temperature. After 15 minutes' stirring at this temperature, it was stirred for 1 hour at room temperature. Then it was cooled to −78° C. and a solution of 19 g 6-{[tert.butyl(dimethyl)silyl]oxy}hexanal in 150 ml THF was added dropwise thereto such that the temperature did not exceed −60° C. After three hours' stirring at −78° C., it was warmed to room temperature. Then 150 ml of a saturated aqueous ammonium chloride solution was added thereto and the mixture was extracted several times with EA. The combined organic phases were washed in succession with water and saturated aqueous common salt solution, dried over sodium sulfate and evaporated in a vacuum. The remaining residue was flash-chromatographed with a solvent system consisting of n-hexane/ethyl acetate (4:1 v/v) on silica gel. Evaporating the product fractions in a vacuum yielded 28.5 g 8-{[tert.butyl(dimethyl)silyl]oxy}-2-hexyl-3-hydroxy-octanoic acid as syn/anti mixture, $^1$H-NMR (400 MHz, CDCl$_3$; selected signals): δ=0.05 (s, 6H), 0.88 (t, 3H), 0.89 (s, 9H), 2.47 (m, 1H), 3.61 (t, 2H), 3.72 and 3.85 (m,1H).

D) 49 ml pyridine was added at 0° C. under a nitrogen atmosphere to a solution of 7.6 ml freshly distilled benzenesulfonic acid chloride in 100 ml dichloromethane. Then a solution of 11.1 g 8-{[tert.butyl(dimethyl)silyl]oxy}-2-hexyl-3-hydroxy-octanoic acid in 100 ml dichloromethane was added dropwise thereto at this temperature. This reaction mixture was left for 20 hours at 4° C. Then the organic phase was washed in succession with water and saturated aqueous common salt solution, dried over sodium sulfate and evaporated in a vacuum. The remaining residue was flash-chromatographed on silica gel, with pure n-hexane, to which a continuously increasing proportion of ethyl acetate was added, being used as mobile solvent. 4.0 g 4-(5-{[tert.butyl(dimethyl)silyl]oxy}pentyl)-3-hexyl-oxetan-2-one was obtained as trans/cis mixture (7:1), $^1$H-NMR (400 MHz, CDCl$_3$): δ=0.05 (s, 6H), 0.89 (t, 3H), 0.89 (s, 9H), 3.16 (m, 1H), 3.61 (t, 2H), 4.21 (m, 1H) (selected signals for trans-isomer); 3.60 (m, 1H), 4.52 (m, 1H) (selected signals for cis-isomer).

E) A solution of 10.97 g tetrabutylammonium fluoride trihydrate in 40 ml THF was added dropwise to a solution of 3.1 g 4-(5-{[tert.butyl(dimethyl)-silyl]oxy}pentyl)-3-hexyl-oxetan-2-one in 40 ml THF under a nitrogen atmosphere at 0° C. and stirred first for 1 hour at this temperature and then for 1 hour at RT. Then the reaction mixture was diluted with ethyl acetate, and the organic phase was washed in succession with water and saturated aqueous common salt solution. The organic phase was dried over sodium sulfate and evaporated in a vacuum. The remaining residue was flash-chromatographed on silica gel with a solvent system consisting of n-hexane/ethyl acetate (9:1 v/v). Evaporating the product fractions in a vacuum yielded 1.9 g 3-hexyl-4-(5-hydroxypentyl)-oxetan-2-one as trans/cis mixture (8:1), $^1$H-NMR (400 MHz, CDCl$_3$): trans: δ=3.17 (m, 1H), 4.22 (m, 1H); cis: δ=3.6 (m, 1H), 4.53 (m, 1H) (characteristic signals of the protons of β-lactone).

F) A solution of 0.3 g 3-hexyl-4-(5-hydroxypentyl)-oxetan-2-one in 5 ml dichloromethane was added dropwise under a nitrogen atmosphere to a solution of 0.45 g phenyl isocyanate in 5 ml dichloromethane at 0° C. Then the solution was stirred for 5 minutes at 0° C. and then for 1 hour at RT. For working-up, the organic phase was washed in succession with water and with saturated aqueous common salt solution, dried over sodium sulfate and evaporated in a vacuum. The remaining residue was flash-chromatographed on silica gel with a solvent system consisting of n-hexane/ethyl acetate (9:1 v/v). 0.4 g 5-(3-hexyl-4-oxo-oxetan-2-yl)pentyl-phenyl carbamate was obtained as trans/cis mixture, $^1$H-NMR (400 MHz, CDCl$_3$) trans: δ=3.17 (m, 1H), 4.22 (m, 1H); cis: δ=3.60 (m, 1H), 4.53 (m, 1H) (characteristic signals of the protons of β-lactone); IR: 3331, 2931, 2859, 1818, 1732, 1600, 1540 cm$^{-1}$.

EXAMPLE 3 cis/trans-5-(3-hexyl-4-oxo-oxetan-2-yl)pentyl-isopropyl carbamate

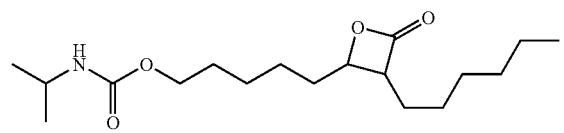

A) 12.4 ml 3,4-dihydro-2H-pyran and 0.7 g p-toluenesulfonic acid were added under a nitrogen atmosphere to a solution of 22.8 g 1,6-hexanediol in 400 ml THF at 0° C.

After stirring for 45 minutes at 0° C., it was allowed to warm to RT. Then a further 6.2 ml 3,4-dihydro-2H-pyran was added thereto and stirred for another hour at RT. It was evaporated in a vacuum, the remaining residue was taken up with dichloromethane, the organic phase was washed in succession with saturated aqueous sodium hydrogen carbonate solution, water and saturated common salt solution and dried over sodium sulfate. Evaporation in a vacuum and flash chromatography of the remaining residue on silica gel with a solvent system which initially consisted of n-hexane/ethyl acetate (9:1 v/v) and was varied by a continuously increased proportion of EA, yielded 18.3 g 6-[(tetrahydro-2H-pyran-2-yl)oxy]hexan-1-ol, $^1$H-NMR (400 MHz, CDCl$_3$): δ=1.34–1.47 (m, 4H), 1.48–1.65 (m, 8H), 1.71 (m, 1H), 1.83 (m, 1H), 3.40 (dt, J=6.6; 9.6 Hz,1H), 3.50 (m, 1H), 3.65 (t, J=6.5 Hz, 2H), 3.74 (dt, J=6.8; 9.6 Hz, 1H), 3.87 (m, 1H), 4.57 (dd, J=2.7; 4.2 Hz, 1H).

B) A solution of 19.7 ml DMSO in 75 ml dry dichloromethane was added dropwise under a nitrogen atmosphere to a solution of 11.6 ml oxalyl chloride in 250 ml dry dichloromethane at −55° C. After five minutes' stirring, a solution of 18.3 g 6-[(tetrahydro-2H-pyran-2-yl)oxy]hexan-1-ol in 150 ml dry dichloromethane was slowly added dropwise thereto at this temperature. After 15 minutes, 81.5 ml triethylamine was added dropwise thereto. Then the reaction mixture was stirred for 15 minutes at −55° C. and then thawed to RT. The organic phase was washed first with water and then with saturated aqueous common salt solution, was separated from the aqueous phase and was dried over sodium sulfate. The drying agent was filtered off, the mixture was evaporated in a vacuum and the remaining residue was flash-chromatographed on silica gel with a solvent system consisting of n-hexane/ethyl acetate (9:1 v/v), the ethyl acetate content of which was continuously increased. 14.1 g 6-[(tetrahydro-2H-pyran-2-yl)oxy]hexanal was obtained, $^1$H-NMR (400 MHz, CDCl$_3$): δ=1.37–1.47 (m, 2H), 1.48–1.75 (m, 9H), 1.77–1.89 (m, 1H), 2.44 (dt, J=1.8; 7.3 Hz, 2H), 3.39 (dt, J=6.4; 9.7 Hz, 1H), 3.50 (m, 1H), 3.74 (dt, J=6.7; 9.7 Hz, 1H), 3.86 (m, 1H), 4.56 (dd, J=2.8; 4.4 Hz, 1H), 9.77 (t, 1.8 Hz, 1H).

C) 96.1 ml of a 1.6 molar solution of n-butyllithium in n-hexane was added dropwise to a solution of 21.6 ml diisopropylamine in 250 ml THF under a nitrogen atmosphere at −70° C. Once this solution had been warmed to 0° C. and had been left at this temperature for 10 minutes, it was cooled to −50° C. and a solution of 12.1 ml octanoic acid in 125 ml THF was slowly added dropwise at this temperature. After 15 minutes' stirring at this temperature, it was stirred for 1 hour at RT. Then it was cooled to −78° C. and a solution of 14 g 6-[(tetrahydro-2H-pyran-2-yl)oxy]hexanal in 125 ml THF was added dropwise thereto. After three hours' stirring at −78° C., it was warmed to RT. Then 150 ml of a saturated aqueous ammonium chloride solution was added thereto and the mixture was extracted several times with EA. The combined organic phases were washed in succession with water and with saturated aqueous common salt solution, dried over sodium sulfate and evaporated in a vacuum. The remaining residue was flash-chromatographed on silica gel with a solvent system consisting of n-hexane/ethyl acetate (4:1 v/v), the proportion of ethyl acetate being continuously increased. Evaporating the product fractions in a vacuum yielded 16.2 g 2-hexyl-3-hydroxy-8-[(tetrahydro-2H-pyran-2-yl)oxy]octanoic acid as syn/anti mixture, $^1$H-NMR (400 MHz, CDCl$_3$): δ=0.88 (m, 3H), 1.25–1.89 (m, 25H), 2.47 (m, 1H), 3.40 (dt, 1H), 3.51 (m, 1H), 3.73 (m, 1H), 3.86 (m, 1H), 4.57 (m, 1H).

D) 50 ml pyridine was added under a nitrogen atmosphere to a solution of 12 ml freshly distilled benzenesulfonic acid chloride in 150 ml dichloromethane at 0° C. Then a solution of 16.2 g 2-hexyl-3-hydroxy-8-[(tetrahydro-2H-pyran-2-yl)oxy]octanoic acid in 100 ml dichloromethane was added dropwise thereto at this temperature. This reaction mixture was left for 20 hours at 4° C. Then the organic phase was washed in succession with water and saturated aqueous common salt solution, dried over sodium sulfate and evaporated in a vacuum. The remaining residue was flash-chromatographed on silica gel, with pure n-hexane, to which a continuously increasing proportion of ethyl acetate (up to 8:2 v/v) had been added, being used as mobile solvent. 10.0 g 3-hexyl-4-{5[(tetrahydro-2H-pyran-2-yl)oxy]pentyl}oxetan-2-one was obtained as diastereomer mixture (2:1), $^1$H-NMR (400 MHz, CDCl$_3$) trans: δ=3.16 (m, 1H), 4.21 (m, 1H); cis: δ=3.59 (m, 1H), 4.53 (m, 1H) (characteristic signals of the protons of β-lactone), IR: 1822, 1465, 1077 cm$^{-1}$ E) 1.89 g 3-hexyl-4-{5[(tetrahydro-2H-pyran-2-yl)oxy]pentyl}oxetan-2-one was dissolved in 58 ml ethanol and 1.46 g pyridinium-p-toluenesulfonate was added thereto. It was stirred for 4 hours at 50° C. and then a further 1.46 g pyridinium-p-toluenesulfonate was added thereto. This reaction mixture was stirred for 1 hour at 50° C. and then for 20 hours at RT. The precipitate was filtered off, the filtrate was evaporated in a vacuum and the remaining residue was flash-chromatographed on silica gel with a solvent system consisting of n-hexane/ethyl acetate (9:1 v/v), the proportion of ethyl acetate of which was continuously increased. Evaporation of the product fractions yielded 1.0 g cis/trans-3-hexyl-4-(5-hydroxypentyl)-oxetan-2-one, which was used without further purification directly for the next reaction.

F) A solution of 0.3 g 3-hexyl-4-(5-hydroxypentyl)-oxetan-2-one in 5 ml dichloromethane was added dropwise under a nitrogen atmosphere to a solution of 0.4 g isopropyl isocyanate in 5 ml dichloromethane at 0° C. Then the solution was stirred for 5 minutes at 0° C. and then for 1 hour at RT. 0.2 ml diisopropylethylamine was added thereto and the mixture was stirred for a further 2 hours at 50° C. It was washed with water and saturated aqueous common salt solution, dried over sodium sulfate and was evaporated in a vacuum. The resulting residue was flash-chromatographed with a solvent system of n-hexane/ethyl acetate (9:1 v/v), the proportion of EE of which was continuously increased to 100%, on silica gel. 0.1 g 5-(3-hexyl-4-oxo-oxetan-2-yl)pentyl-isopropyl carbamate was obtained as trans/cis mixture (2:1), $^1$H-NMR (400 MHz, CDCl$_3$): trans: δ=3.16 (m, 1H), 4.21 (m, 1H); cis: δ=3.60 (m, 1H), 4.52 (m, 1H) (characteristic signals of the protons of β-lactone); IR: 3321, 2930, 1813, 1687, 1538, 1468 cm$^{-1}$.

EXAMPLE 4 trans-5-(3-hexyl-4-oxo-oxetan-2-yl)-butyl-benzyl carbamate

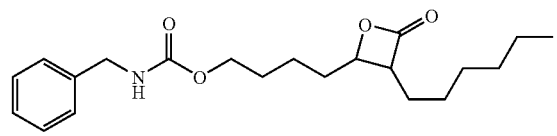

A) 94.0 ml triethylamine was added to 50.0 g 2-mercaptopyridine, dissolved in 1 l dichloromethane, at 0° C. under a nitrogen atmosphere. 73.2 g octanoyl chloride in 200 ml dichloromethane was added thereto within 10 minutes.

After removal of the cooling, it was stirred for 90 minutes at RT and then 600 ml water was added thereto. Once the organic phase had been separated, the aqueous phase was extracted three times with 200 ml dichloromethane each time. The combined organic phases were dried over magnesium sulfate and then evaporated in a vacuum. The remaining residue was flash-chromatographed on silica gel with n-pentane/diethyl ether (1:1 v/v). 101.6 g thiooctanoic acid-S-pyridin-2-yl ester was obtained, $^1$H-NMR (400 MHz, CDCl$_3$): δ=0.88 (t, J=6.9 Hz, 3H), 1.23–1.40 (m, 8H), 1.69–1.76 (m, 2H), 2.70 (t, J=7.5 Hz, 2H), 7.28 (ddd, J=7.5; 4.8; 1.1 Hz, 1H), 7.61 (dt, J=0.8; 7.8 Hz, 1H), 7.73 (dt, J=1.9; 7.7 Hz, 1H), 8.62 (ddd, J=4.8; 1.8; 0.7 Hz, 1H).

B) 97.6 ml of a lithium hexamethyl disilazide solution (1M in THF) in 420 ml THF was cooled to −10° C. under a nitrogen atmosphere, 12.6 ml DMF and 22.7 ml triethylamine were added thereto in succession and the mixture was stirred for 10 minutes. Then 24.5 g triethylsilyl chloride in 50 ml THF was added thereto and the reaction mixture was cooled to −78° C. Then 19.3 g thiooctanoic acid-S-pyridin-2-yl ester in 50 ml THF was slowly added dropwise thereto and the mixture was stirred for 1 hour at −78° C.

After removal of the cooling, the reaction mixture was warmed to 10° C. within one hour and 800 ml water was added thereto. After multiple extractions with diethyl ether, the organic phase was dried over magnesium sulfate and evaporated in a vacuum. The remaining residue was quickly flash-chromatographed on silica gel with a solvent system consisting of n-pentane/diethyl ether (9:1 v/v). Evaporating the product fractions yielded 25.6 g 2-({(1 E)-1-[(triethylsilyl)oxy]oct-1-en-1-yl}thio)pyridine, $^1$H-NMR (400 MHz, CDCl$_3$): δ=0.60–0.69 (m, 6H), 0.84–0.91 (m, 12H), 1.24–1.43 (m, 8H), 2.18 (q, J=7.2 Hz, 2H), 5.38 (t, J=7.3 Hz, 1H), 6.99 (ddd, J=7.4; 4.9; 1.0 Hz, 1H), 7.34 (dt, J=1.0; 8.1 Hz, 1H), 7.54 (ddd, J=8.1; 7.4; 1.9; Hz, 1H), 8.42 (ddd, J=4.9; 1.9; 0.9 Hz, 1H).

C) 37.9 g 5-{[tert.butyl(dimethyl)silyl]oxy}pentanal (for preparation see Example 2B)) was added to a suspension of 34.0 g anhydrous zinc chloride in 800 ml dichloromethane at RT and under a nitrogen atmosphere and the mixture was stirred for 15 minutes. Then 55.9 g 2-({(1E)-1-[(triethylsilyl)oxy]oct-1-en-1-yl}thio)pyridine was added thereto and the reaction mixture was stirred for 40 hours at RT. Then saturated aqueous sodium hydrogen carbonate solution was added thereto, the phases were separated and the aqueous phase was extracted three times with dichloromethane. The combined organic phases were dried over magnesium sulfate and evaporated in a vacuum to a volume of approx. 500 ml. 47.7 g copper dibromide was added to this solution and it was stirred for 90 minutes at RT. Then the resulting suspension was filtered over silica gel, rinsing being performed with dichloromethane. Evaporation in a vacuum and flash chromatography of the remaining residue on silica gel with a solvent system consisting of n-pentane/diethyl ether (33:1 v/v) yielded 17.8 g 4-(5-{[tert.butyl(dimethyl)silyl]oxy}butyl)-3-hexyl-oxetan-2-one as pure trans product, $^1$H-NMR (400 MHz, CDCl$_3$): δ=0.04 (s, 6H), 0.85–0.90 (m, 12H), 1.22–1.92 (m, 16H), 3.16 (ddd, J=8.8; 6.5; 3.9 Hz, 1H), 4.21 (ddd, J=7.2; 6.1; 4.0 Hz, 1H).

D) 17.8 g of the compound obtained above was dissolved in 200 ml THF in a PET vessel, 10 ml HF/pyridine complex was added thereto and the mixture was then stirred overnight at RT. Then the reaction mixture was filtered over silica gel and rinsed with diethyl ether. The solvent was evaporated in a vacuum and the remaining residue was flash-chromatographed with a solvent system consisting of n-pentane/diethyl ether (1:1 v/v) on silica gel. Drying the product fractions yielded 10.6 g 3-hexyl-4-(5-hydroxybutyl)-oxetan-2-one as pure trans product, $^1$H-NMR (400 MHz, CDCl$_3$): δ=0.89 (t, J=6.3 Hz, 3H), 1.29–1.93 (m, 16H), 2.14 (s br, 1H), 3.19 (ddd, J=8.6; 6.6; 3.9 Hz, 1H), 3.65 (t, J=6.3 Hz, 2H), 4.24 (ddd, J=7.4; 5.6; 4.0 Hz, 1H).

E) A solution of 0.3 g 3-hexyl-4-(5-hydroxybutyl)-oxetan-2-one in 5 ml dichloromethane was added dropwise to a solution of 0.26 g benzyl isocyanate in 5 ml dichloromethane under a nitrogen atmosphere at 0° C. The mixture was then stirred for 10 minutes at 0° C. and then for 20 hours at RT. The organic phase was washed in succession with water and saturated aqueous common salt solution, dried over sodium sulfate and was evaporated in a vacuum. The remaining residue was flash-chromatographed with a solvent system consisting of n-hexane/ethyl acetate (3:2 v/v) on silica gel and the combined product fractions were then recrystallised from a mixture of n-hexane/EA. 0.4 g of the title compound was obtained as a pure trans product, m.p. 50.9–52.5° C.; $^1$H-NMR (400 MHz, CDCl$_3$): δ=0.89 (t, 3H), 3.17 (m, 1H), 4.12 (t, 2H), 4.20 (m, 1H), 4.36 (d, 2H), 4.94 (s br, 1H), 7.23–7.37 (m, 5).

EXAMPLE 5 trans-5-(3-benzyl-4-oxo-oxetan-2-yl)pentyl-(4-acetylphenyl)carbamate

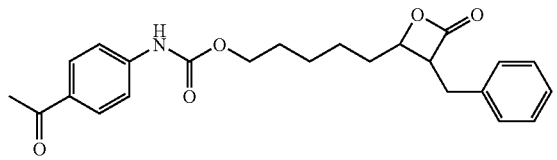

A) 13.7 ml of a 1.6 M n-butyllithium solution in n-hexane was added dropwise to a solution of 2.2 g diisopropylamine in 15 ml THF at −60° C. It was allowed to thaw to −40° C. for 30 minutes and was then cooled to −75° C. A solution of 2.8 g 8-benzyloxy-3-hydroxy-octanoic acid-methyl ester (for preparation see Example 1 C)) was added dropwise to this reaction mixture slowly and then was stirred at −55° C. for 3 hours. It was cooled to −75° C., 2 ml HMPT was added and the mixture was stirred again for 30 minutes. Then 3.42 g benzyl bromide, dissolved in 3 ml THF, was slowly added dropwise and the mixture was warmed to RT over a period of 20 hours. It was taken up with ethyl acetate, and the organic phase was washed in succession with water, aqueous potassium hydrogen sulfate solution and once again water, and then dried over sodium sulfate. The remaining residue was flash-chromatographed with a mixture of n-hexane/ethyl acetate (9:1 v/v, changed continuously to 3:1 v/v), on silica gel. Drying of the product fractions yielded 2.7 g diastereomerically pure 2-benzyl-8-(benzyloxy)-3-hydroxy-octanoic acid methyl ester, $^1$H-NMR (200 MHz, CDCl$_3$): δ=1.2–1.7 (m, 8H), 2,57 (d, 1H), 2.72 (ddd, 1H), 2.90–3.10 (m, 2H), 3.45 (t, 2H), 3.61 (s, 3H), 4.49 (s, 2H).

B) A solution of 1.83 g lithium hydroxide in 30 ml water was added to a solution of 10.8 g 2-benzyl-8-(benzyloxy)-3-hydroxy-octanoic acid methyl ester in 90 ml ethanol. Once this reaction mixture had been stirred for 18 hours at RT, 1 M citric acid was added thereto and excess solvent was evaporated in a vacuum. The remaining residue was taken up in EA, the organic phase was washed in succession with aqueous potassium hydrogen sulfate solution and water and finally dried over sodium sulfate. Evaporating in a vacuum yielded a solid residue which was recrystallised from n-hexane/ethyl acetate (1:1 v/v). 9.31 g diastereomerically pure 2-benzyl-8-(benzyloxy)-3-hydroxy-octanoic acid was obtained, mp. 66–67° C.; IR: 3233, 2932, 2849, 1706, 1454, 1125 cm$^{-1}$.

C) 9.31 g 2-benzyl-8-(benzyloxy)-3-hydroxy-octanoic acid was dissolved in 52 ml pyridine under a nitrogen atmosphere and 5.1 g benzenesulfonic acid chloride was added thereto at −20° C. Then it was stirred for 2 hours at 0° C. and then for 48 hours at 4° C. The reaction mixture was diluted with diethyl ether, was washed in succession three times with water and once each with 1M citric acid and water and the organic phase was dried over sodium sulfate. The solvent was evaporated in a vacuum and the remaining residue was then flash-chromatographed on silica gel with a solvent system consisting of n-hexane/ethyl acetate (initially 9:1 v/v, then continuously changing to 3:1 v/v). Drying the product fractions yielded 7.2 g trans-3-benzyl-4-[5-(benzyloxy)pentyl]oxetan-2-one, IR: 2933, 2858, 1816, 1454, 1114 cm$^{-1}$.

D) 7.1 g of the product obtained above was dissolved in 200 ml ethyl acetate and 0.7 g of a 10%-strength Pd/C catalyst was added thereto. Then it was hydrogenated for 5 hours at 2.5 bar hydrogen pressure. After filtering off the catalyst, it was evaporated in a vacuum. 4.9 g 3-benzyl-4-(5-hydroxypentyl)oxetan-2-one was obtained, $^1$H-NMR (400 MHz, CDCl$_3$): δ=1.08–1.34 (m, 5H), 1.47 (m, 2H), 1.62 (m, 1H), 1.80 (m, 1H), 3.00 (dd, J=9.4; 14.3 Hz, 1H), 3.18 (dd, J=5.7; 14.3 Hz, 1H), 3.46 (m, 1H), 3.58 (t, 2H), 4.28 (m, 1H), 7.19 (m, 2H), 7.26 (m, 1H), 7.32 (m, 2H).

E) A solution of 0.3 g 3-benzyl4-(5-hydroxypentyl)-oxetan-2-one in 5 ml dichloromethane was added under a nitrogen atmosphere to a solution of 0.29 g 4-acetylphenyl isocyanate in 10 ml dichloromethane at 0° C. It was then stirred for 30 minutes at 0° C. and then for 2 hours at RT. 0.21 ml of diisopropylethylamine was added and the mixture was stirred for 2 days at RT. Then it was taken up with dichloromethane, the organic phase was washed in succession with water and saturated aqueous common salt solution, dried over sodium sulfate and evaporated in a vacuum. The remaining residue was flash-chromatographed on silica gel with a solvent system consisting of n-hexane/ethyl acetate (3:2 v/v). Drying of the product fractions yielded 0.4 g of the title compound, m.p. 104–106° C.; $^1$H-NMR (400 MHz, CDCl$_3$): δ=1.1–1.4 (m, 4H), 1.54–1.68 (m, 3H), 1.80 (m, 1H), 2.56 (s, 3H), 3.00 (dd, J=9.5; 14.3 Hz, 1H), 3.18 (dd, J=5.7; 14.3 Hz, 1H), 3.47 (m, 1H), 4.12 (t, 2H), 4.28 (m, 1H), 6.84 (s br, 1H), 7.19 ("d", 2H), 7.25 (m, 1H), 7.32 ("t", 2H), 7.48 (d, 2H), 7.93 ("d", 2H).

EXAMPLE 6

(2S,3S)-5-(3-hexyl-4-oxo-oxetan-2-yl)-pentyl-(4-phenoxyphenyl)-carbamate

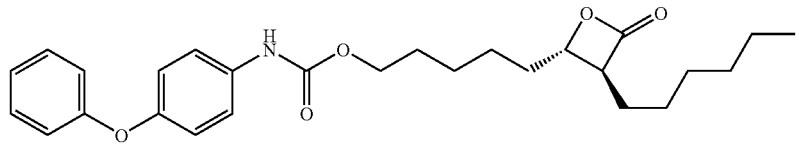

A) First 14.9 g pyridinium chlorochromate and then some Celite® was added to a solution of 17.7 g 8-benzyloxy-3-hydroxy-octanoic acid methyl ester (for preparation see Example 1C)) in 350 ml dichloromethane. It was stirred overnight at RT, a further 15.0 g pyridinium chlorochromate was added and the mixture was heated to boiling for 10 minutes under reflux cooling. Then it was again stirred overnight at RT, then 400 ml diethyl ether was added and it was filtered over Celite®. The filtrate was evaporated in a vacuum and the remaining residue was flash-chromatographed with a solvent system consisting of n-heptane/ethyl acetate (2:1 v/v) on silica gel. Drying the product fractions yielded 13.0 g 8-benzyloxy-3-oxo-octanoic acid methyl ester.

B) 0.106 g benzene ruthenium(II) chloride dimer was added under an argon atmosphere to 0.26 g (S)-(−)-2,2'-bis-(diphenylphosphino)-1,1'-binaphthyl. 8 ml DMF, which had previously been purified by freezing and thawing three times, was added thereto. The resulting reaction mixture was heated for 15 minutes to 115° C. and after cooling to RT was evaporated in a vacuum at 65° C. A solution of 13 g 8-benzyloxy-3-oxo-octanoic acid methyl ester in 35 ml methanol was added to the remaining brown solids and the reaction solution was then transferred into an autoclave using a syringe. The solution was hydrogenated at 70° C. for 6 hours at a hydrogen pressure of 4.2 bar, then evaporated in a vacuum and the remaining residue was flash-chromatographed with a solvent system consisting of n-heptane/ethyl acetate (2:1 v/v) on silica gel. Drying the product fractions yielded 10.7 g (S)-8-benzyloxy-3-hydroxy-octanoic acid methyl ester as a slightly yellowish oil. The enantiomeric purity was determined using a Chiralpak AD-H column from Daicel. A solvent system consisting of n-heptane/isopropanol (9:1 v/v) was used as mobile phase; the flow rate was 1 ml/min. Under these conditions, a retention time of 32.297 minutes was measured.

C) 48 ml of a 1.6 molar solution of n-butyllithium in n-hexane was added dropwise to a solution of 7.7 g diisopropylamine in 60 ml THF at −60° C. It was allowed to thaw to −40° C. for 30 minutes and was then cooled to −78° C. A solution of 9.8 g (S)-8-benzyloxy-3-hydroxy-octanoic acid methyl ester in 10 ml THF was slowly added dropwise to the resulting reaction mixture and the mixture was warmed to −40° C. for 3 hours. Then it was cooled again to −75° C. and first 8 ml DMPH, dissolved in 8 ml THF, and then 14.8 g n-hexyl iodide were added dropwise thereto. The resulting reaction mixture was left to thaw to RT overnight, diluted with ethyl acetate, and the organic phase was washed in succession with water, dilute aqueous potassium hydrogen sulfate solution and saturated aqueous common salt solution. The organic phase was dried over sodium sulfate, evaporated in a vacuum and the remaining residue was flash-chromatographed on silica gel with a solvent system consisting of n-hexane/ethyl acetate (9:1 v/v), to which ethyl acetate was added gradually up to a composition of 3:1 (v/v). Drying the product fractions yielded 4.0 g (S,S)-8-benzyloxy-2-hexyl-3-hydroxy-octanoic acid methyl ester, $[\alpha]_D=-12.60°$ (c=25.7 mg in 2 ml methanol); IR: 2928, 2856, 1733, 1454, 1164, 1100 cm$^{-1}$.

D) 5.5 g (S,S)-8-benzyloxy-2-hexyl-3-hydroxy-octanoic acid methyl ester was dissolved in 40 ml ethanol, 0.97 g lithium hydroxide hydrate in 13 ml water was added thereto and the mixture was stirred for 24 hours at RT. Then dilute aqueous potassium hydrogen sulfate solution was added thereto and excess solvent was evaporated in a vacuum. It was taken up with EA, the organic phase was washed in succession with dilute aqueous potassium hydrogen sulfate solution and water, it was separated from the aqueous phase and dried over sodium sulfate. After evaporating in a vacuum and drying in an oil pump vacuum, 5.4 g (S,S)-8-benzyloxy-2-hexyl-3-hydroxyoctanoic acid was obtained as a slightly yellowish oil, which was used without further purification for the next reaction, $[\alpha]_D=-14.23°$ (c=21.5 mg in 2 ml methanol); IR: 2928, 2856, 1706, 1454, 1100 cm$^{-1}$.

E) 5.4 g (S,S)-8-benzyloxy-2-hexyl-3-hydroxy-octanoic acid was dissolved in 30 ml pyridine and 2.99 g benzenesulfonic acid chloride was added thereto at −20° C. The mixture was warmed to 0° C. within 2 hours and then left for 48 hours at 4° C. It was diluted with diethyl ether and the organic phase was washed in succession three times with ice-cold water, 0.5 M citric acid and saturated aqueous common salt solution. The organic phase was dried over sodium sulfate and evaporated in a vacuum. The remaining residue was flash-chromatographed with a solvent system consisting of n-hexane/ethyl acetate (initially 9:1 v/v, then continuously changing to 3:1 v/v), on silica gel. Drying the product fractions yielded 2.6 g (S,S)-4-[5-(benzyloxy)pentyl]-3-hexyl-oxetan-2-one, $[\alpha]_D=-23.21°$ (c=16.6 mg in 2 ml chloroform), IR: 2929, 2857, 1818, 1455, 1117 cm$^{-1}$.

F) 2.5 g (S,S)-4-[5-(benzyloxy)pentyl]-3-hexyl-oxetan-2-one was dissolved in 100 ml ethyl acetate, and 0.25 g of a 10%-strength Pd/C-catalyst was added thereto. Then it was hydrogenated at a hydrogen pressure of 2.5 bar for 5 hours. The catalyst was filtered off, excess solvent was evaporated in a vacuum and it was then dried in an oil pump vacuum. 1.86 g (S,S)-4-[5-hydroxypentyl]-3-hexyl-oxetan-2-one was obtained as oil, $[\alpha]_D=-37.5°$ (c=1 in EA).

G) A solution of 0.6 g (S,S)-4-[5-hydroxypentyl]-3-hexyl-oxetan-2-one in 10 ml dichloromethane was added dropwise to a solution of 0.78 g 4-phenoxyphenyl isocyanate in 10 ml dichloromethane at 0° C. under a nitrogen atmosphere. The mixture was then stirred for 15 minutes at 0° C. and then for 2 hours at RT. 0.43 ml diisopropylethylamine was added and the mixture was stirred for 2 days at RT. Then it was taken up with dichloromethane, the organic phase was washed in succession with water and saturated aqueous common salt solution, dried over sodium sulfate and evaporated in a vacuum. The remaining residue was flash-chromatographed with a solvent system consisting of n-hexane/ethyl acetate (4:1 v/v) on silica gel. Drying of the product fractions yielded 0.74 g of the title compound, m.p. 73–74° C.; $[\alpha]_D=-21.5°$ (c=1 in EA); $^1$H-NMR (400 MHz, CDCl$_3$): δ=0.89 (t, 3H), 1.2–1.9 (m, 18H), 3.18 (m, 1H), 4.17 (t, 2H), 4.22 (m, 1H), 6.55 (s, br, 1H), 6.96–7.00 (m, 4H), 7.07 ("t", 1H), 7.28–7.37 (m, 4H).

The compounds of Formula I listed in the following Table 3 can also be prepared according to the processes described in the foregoing examples or according to processes analogous thereto:

TABLE 3

Further compounds of Formula I

| Ex. No. | R$^1$ | R$^2$ | n | trans:cis |
|---|---|---|---|---|
| 7 | Phenyl | n-hexyl | 3 | cis |
| 8 | Benzyl | n-hexyl | 5 | 3:1 |
| 9 | 4-ethoxyphenyl | n-hexyl | 5 | 3:1 |
| 10 | Benzoyl | n-hexyl | 5 | 3:1 |
| 11 | Phenylethyl | n-hexyl | 5 | 6:1 |
| 12 | n-butyl | n-hexyl | 5 | 2:1 |
| 13 | 3,4-dichlorophenyl | n-hexyl | 5 | 12:1 |
| 14 | 4-fluorophenyl | n-hexyl | 5 | 3.5:1 |
| 15 | 4-phenoxyphenyl | n-hexyl | 4 | trans |
| 16 | 2-isopropylphenyl | n-hexyl | 4 | trans |
| 17 | 2-nitrophenyl | n-hexyl | 4 | trans |
| 18 | 4-benzylphenyl | n-hexyl | 4 | trans |
| 19 | 2-ethyloxycarbonylphenyl | benzyl | 5 | trans |
| 20 | Octadecanyl | n-hexyl | 4 | trans |
| 21 | 2-trifluoromethylphenyl | n-hexyl | 4 | trans |
| 22 | 4-heptyloxyphenyl | n-hexyl | 4 | trans |
| 23 | 2,5-dimethoxyphenyl | benzyl | 5 | trans |

All the compounds listed in Table 3 are racemic.

EXAMPLE I

Capsules containing trans-(3-hexyl-4-oxo-oxetan-2-yl)-pentyl-(4-phenoxyphenyl)-carbamate Capsules with the following composition per capsule were produced:

| | |
|---|---|
| trans-(3-hexyl-4-oxo-oxetan-2-yl)-pentyl-(4-phenoxyphenyl)-carbamate | 20 mg |
| Corn starch | 60 mg |
| Lactose | 300 mg |
| Ethyl Acetate | q.s. |

The active substance, the corn starch and the lactose were processed into a homogeneous pasty mixture using ethyl acetate. The paste was ground and the resulting granules were placed on a suitable tray and dried at 45° C. in order to remove the solvent.

The dried granules were passed through a crusher and mixed in a mixer with the further following auxiliaries:

| | |
|---|---|
| Talcum | 5 mg |
| Magnesium stearate | 5 mg |
| Corn starch | 9 mg | and then poured into 400 mg capsules (=capsule size 0).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A compound corresponding to formula I,

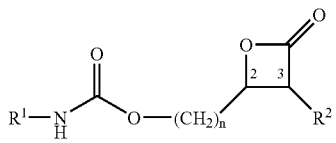

wherein
R$^1$ is
  C$_{1-18}$-alkyl, one or two alkyl-chain carbon atoms of which are optionally replaced by oxygen or sulfur;
  phenyl-C$_{0-18}$-alkyl, the phenyl group of which is optionally substituted one or two times by halogen, trifluoromethyl, nitro, C$_{1-8}$-alkyl, C$_{1-8}$-alkoxy, C$_{1-6}$-alkylcarbonyl, C$_{1-6}$-alkoxycarbonyl, phenyl, benzyl or phenoxy, and one or two alkyl-chain carbon atoms of which are optionally replaced by oxygen or sulfur;
  C$_{3-7}$-cycloalkyl-C$_{0-18}$-alkyl, one or two alkyl-chain carbon atoms of which are optionally replaced by oxygen or sulfur, or
  benzoyl;
R$^2$ is
  C$_{1-12}$-alkyl, one or two alkyl-chain carbon atoms of which are optionally replaced by oxygen or sulfur;
  phenyl-C$_{1-18}$-alkyl, the phenyl group of which is optionally substituted once or twice by halogen, C$_{1-4}$-alkyl, C$_{1-4}$-alkoxy, benzyl or phenoxy, and one or two alkyl-chain carbon atoms of which are optionally replaced by oxygen or sulfur; or
  C$_{3-7}$-cycloalkyl-C$_{0-18}$-alkyl, one or two alkyl-chain carbon atoms of which are optionally replaced by oxygen or sulfur,
and
n is a whole number from 2 to 8.

2. A compound according to claim 1, wherein R$^1$ is phenyl-C$_{0-2}$-alkyl, the phenyl group of which is optionally substituted by C$_{1-4}$-alkyl, C$_{1-4}$-alkoxy or phenoxy.

3. A compound according to claim 1, wherein R$^2$ is C$_{2-6}$-alkyl, the alkyl-chain carbon atoms of which are optionally replaced 1 or 2 times by at least one of oxygen and sulfur.

4. A compound according to claim 1, wherein n is a whole number from 2 to 5.

5. A compound according to claim 1, selected from the group consisting of:
  5-(3-hexyl4-oxo-oxetan-2-yl)-pentyl-(phenoxyphenyl)-carbamate, and
  4-(3-hexyl4-oxo-oxetan-2-yl)-butyl-(phenoxyphenyl)-carbamate.

6. A compound according to claim 1, wherein the substituents of the carbon in the 2-position of the lactone ring and the substituents of the carbon in the 3-position of the lactone ring adopt the trans position relative to one another.

7. A composition of matter comprising a pharmacologically effective amount of a compound according to claim 1 and at least one pharmaceutical carrier, auxiliary or excipient.

8. A method of treating or inhibiting obesity or an obesity-associated condition selected from the group consisting of metabolic syndromes and cardiovascular diseases in a patient in need thereof, said method comprising administering to said patient an pharmaceutically effective amount of a compound according to claim 1.

9. A method according to claim 8, wherein a metabolic syndrome selected from the group consisting of hypertension, insulin resistance, Type II diabetes mellitus, dyslipoproteinaemia and hyperuricaemia, or a cardiovascular disease selected from the group consisting of coronary heart disease, cerebrovascular disease and peripheral occlusive arterial disease, is treated.

10. A process for the preparation of a compound corresponding to formula I,

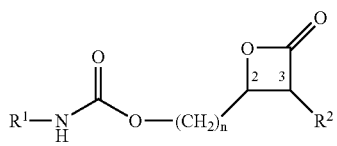

wherein
R$^1$ is C$_{1-18}$-alkyl, the alkyl-chain carbon atoms of which are optionally replaced 1–2 times by oxygen and/or sulfur; phenyl-C$_{0-18}$-alkyl, the phenyl group of which is optionally substituted 1–2 times by halogen, trifluoromethyl, nitro, C$_{1-8}$-alkyl, C$_{1-8}$-alkoxy, C$_{1-6}$-alkylcarbonyl, C$_{1-6}$-alkoxycarbonyl, phenyl, benzyl and/or phenoxy and the alkyl-chain carbon atoms of which are optionally replaced 1–2 times by oxygen and/or sulfur; C$_{3-7}$-cycloalkyl-C$_{0-18}$-alkyl, the alkyl-chain carbon atoms of which are optionally replaced 1–2 times by oxygen and/or sulfur, or benzoyl;
R$^2$ is C$_{1-12}$-alkyl, the alkyl-chain carbon atoms of which are optionally replaced 1–2 times by oxygen and/or sulfur; phenyl-C$_{1-18}$-alkyl, the phenyl group of which is optionally substituted 1–2 times by halogen, C$_{1-4}$-alkyl, C$_{1-4}$-alkoxy, benzyl and/or phenoxy and the alkyl-chain carbon atoms of which are optionally replaced 1–2 times by oxygen and/or sulfur; or C$_{3-7}$-cycloalkyl-C$_{0-18}$-alkyl, the alkyl-chain carbon atoms of which are optionally replaced 1–2 times by oxygen and/or sulfur, and
n is a whole number from 2 to 8;
said method comprising reacting a compound corresponding to formula II,

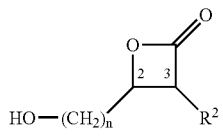

wherein R$^2$ and n have the above meanings,
with a compound corresponding to formula III, $$R^1-N=C=O$$

wherein R$^1$ has the above meaning.

* * * * *